United States Patent [19]
Pardikes

[11] Patent Number: 5,653,915
[45] Date of Patent: Aug. 5, 1997

[54] METHOD OF PREPARING POLYMER SUCCINIC ANHYDRIDE

[76] Inventor: Dennis G. Pardikes, 12811 S. 82nd St., Palos Park, Ill. 60464

[21] Appl. No.: 438,411

[22] Filed: May 10, 1995

[51] Int. Cl.$^6$ .............................. B01J 13/00; D21H 17/43
[52] U.S. Cl. ......................... 252/314; 162/168.1; 252/312
[58] Field of Search ....................... 252/312, 314; 162/168.1

[56] References Cited

U.S. PATENT DOCUMENTS

| | | | |
|---|---|---|---|
| 2,233,965 | 3/1941 | Strovink | 137/7 |
| 3,102,064 | 8/1963 | Wurzburg et al. | 162/158 |
| 4,040,900 | 8/1977 | Mazzarella et al. | 162/158 |
| 4,545,855 | 10/1985 | Sweeney | 162/158 |
| 4,545,856 | 10/1985 | Sweeney | 162/158 |
| 4,606,773 | 8/1986 | Novak | 252/314 X |
| 4,859,720 | 8/1989 | Flesher et al. | 523/332 |
| 5,219,912 | 6/1993 | Takahashi et al. | 162/168.1 X |
| 5,323,017 | 6/1994 | Pardikes | 250/573 |

Primary Examiner—Richard D. Lovering
Attorney, Agent, or Firm—Laff, Whitesel, Conte & Saret, Ltd.

[57] ABSTRACT

The invention is a paper coating system which introduces ASA particles having sizes in the sub-micron region into an emulsifier without shearing the emulsifier. The system has a continuous output—as distinguished from a batch system. The system comprises a variable speed low pressure starch metering pump, a variable speed high pressure ASA metering pump, a high pressure atomizing nozzle assembly, and a manifold which brings the starch and the atomized ASA flow together. The high nozzle pressure breaks up or atomizes the ASA into minute sub-micron particles that are evenly distributed throughout the starch to form a nearly perfect oil in water emulsion. By controlling the nozzle pressure, the proper particle size can be produced quite easily. An optical monitoring device that uses a coherent (laser) light source continuously measures and validates the quality of the ASA emulsion.

11 Claims, 4 Drawing Sheets

METHOD OF PREPARING POLYMER SUCCINIC ANHYDRIDE

This invention relates to means for and methods of preparing and applying a polymer alkenyl succinic anhydride "ASA," also known as "SIZING", especially for use in paper coatings used by the paper making industry.

When added to pulp stock during a paper making process, a hydrocarbon based ASA polymer material forms a protective barrier, resists moisture intrusion into the paper, and provides a conditioned surface for the application of inks to paper.

In greater detail, alkenyl succinic anhydride ("ASA") is an alkene chain which is reacted with maleic anhydride to form the ASA structure which is effective for paper sizing. At room temperature, ASA is a yellow, oily liquid with extremely low water solubility, and with an extremely high hydrophobic level. A recent pertinent article on ASA is entitled *"A Review of Paper Sizing Using Alkyl Ketene Dimer Versus Alkenyl Succinic Anhydride"* by Kevin T. Hodgson, published in the Journal APPITA, Vol. 47, No. 5, pages 402–404.

Paper producers manufacture paper under neutral or alkaline wet end conditions which requires sizing agents that are effective at higher pH values. In response to these requirements, "reactive" sizes have been developed which can produce acceptable sizing performance under alkaline conditions. These compounds have the ability to chemically react with the cellulose of the paper in order to permanently establish the necessary orientation for sizing. Sizing agents impart various degrees of liquid repellency to paper products by altering the wettability of the cellulose fibres which make up the sheet. The reaction rate Of ASA with cellulose is very rapid, and does not require external heat, which results in a rapid sizing of ASA treated paper.

ASA emulsions are stabilized either by cationic starches or by proprietary synthetic polymers. Regardless of whether a cationic starch or a synthetic polymer is used, an additional surfactant is required in the emulsification step. The surfactant provides a boundary layer shear to the ASA particles. This surfactant is normally a non-ionic alkyl phenol ethoxylate. It is thought that the surfactant acts as a rewetting agent on the fibre surfaces, partially defeating the purpose of the sizing agent. Thus, the desired situation is to minimize the amount of added surfactant. For convenience of expression, any and all suitable emulsifiers will hereinafter be called "starch".

The process of applying ASA to paper involves the creation of a high quality emulsion of ASA and an emulsification agent. Usually, emulsification is done on-site by one of two methods. One is a low shear venturi-type emulsifier, but the more common emulsification system is a high shear turbine.

The ASA is insoluble in water and must be added to the furnish as an emulsion. The emulsion should be a stable mixture of two immiscible liquids, (ASA and water soluble polymers), one of which is uniformly dispersed in the other. It might be helpful to visualize the emulsion as being somewhat like many tiny droplets of oil suspended in water. The natural or synthetic based polymers solutions (used in the emulsification process) constitute an external or continuous phase. The ASA droplets form the internal or dispersed phase, the droplets being sometimes called "particles" hereinafter.

The success of the sizing is directly related to the quality of the emulsion (ASA particle size). A high size retention is mandatory in any ASA sizing system. If the ASA colloidal particle size is not small enough, there is a less stable emulsion and a lower retention of the size. A high retention means less recirculation of ASA in a white water system and fewer problems associated with hydrolyzed ASA which forms a gum like particle called a "stickie".

The size (diameter) of these ASA particles (droplets) is one of the more critical parameters in the inventive process. The conflict is to make the particles as small as possible without breaking the molecules of the starch. In general, the smaller the particles, the better, a useful range being about $0.1\,\mu$–$3.0\,\mu$; with a range of about $0.5\,\mu$–$1.5\mu$ preferred. One of the reasons why smaller particle size is so important is that it does less damage to paper making machines which tend to gum-up, ("stickies"), if the particle size is too large.

Because the internal phase is made up of the ASA, the emulsion is classified as an oil in water ("O/W") emulsion. The two most common natural polymer emulsifiers (external phase) are corn and potato starch which are chemically modified to enhance their cationic charge characteristics. The starch surrounds and protects the ASA thus encapsulating the ASA to keep it from hydrolyzing. In effect, the starch is the protective barrier for the particles of oil (ASA) to be spread on the paper. The oil is a covering coating which makes the paper water resistant and receptive to ink.

The production of a quality ASA emulsion is critical to the success of an ASA sizing process. Low quality ASA emulsions are not only less efficient, but also cause many operational problems. One of the most distinct features of internal sizing with ASA is that emulsification must be done on site because the ASA is unstable after it is emulsified with water. The rate of the ASA reaction with water is very fast; therefore, the emulsion must be used quickly in order to avoid the formation of hydrolyzates. Hence, there is a need for the invention, which is a relatively small machine which can be installed on site and operated by people with little or no special training.

In an exemplary mill application, the ASA and starch (or other suitable emulsifier) are metered through an emulsification unit designed to impart enough energy to the mixture to create a suitable and stable emulsion. The emulsion is then metered onto the paper machine by way of separate tanks or pumps. There the ASA emulsion combines with the furnish.

The commercial preparation of an ASA emulsion often involves a use of a regenerative turbine pump to emulsify the ASA. In one prior art example, the ASA (metered through a positive displacement pump) is combined with water or starch, or both, at the suction side of a regenerative turbine pump. The starch and water solution (3–4% by weight) is mixed with ASA inside the turbine or centrifugal pump at pressures above 200 psi and below 300 psi in order to impart a high degree of shear to the mixture as it departs from the pump. The use of such a high pressure drop pump severely degrades the emulsifier and makes the system much more complicated, expensive, and difficult to use. Therefore, a surfactant is used to reduce the need for a high pressure drop pump. However, the addition of surfactant tends to reduce the desired end results. Accordingly, a principal effort is to limit the amount of surfactant required, and to keep the surfactant under a maximum of 4% by weight, a useful range of surfactant being 0–4% by weight, while holding the shear caused by the high pressure drop turbine pump to levels which still promote small ASA particle size.

The composition of most surfactants is a trade secret closely held by the manufacturer. However, the characteristics of the surfactants are widely publicized. Therefore, it is extremely easy to select a suitable surfactant even if its composition is not fully known. From the viewpoint of someone practicing this invention, the customer usually prescribes not only the surfactant to use along with an identification of the polymer to be processed, but also supplies a blend with the surfactant already in the ASA.

The ratio of ASA to starch is initially set at approximately 8:1. Subsequent starch additions downstream of the ASA emulsion, increases the ratio to approximately 30:1. For the same energy input, a higher starch to ASA ratio usually produces smaller particles. In a separate laboratory analysis, the ASA particle can be optically checked to determine an average particle size and particle size distribution.

The prior art and other similar methods of preparing an emulsified ASA have the following distinct disadvantages:
1. Large particle size
2. Shearing of the emulsifier
3. Limited and/or non-existent sub-micron particle size capability
4. Particle size changes with fluctuations in emulsifier flow rates and viscosities
5. Lack of on-line emulsion particle quality verification
6. Large and expensive machinery
7. Exposure of critical system components to thermal shock failure For many years, the industry goal has been to produce an ASA particle size at 1 micron. With systems that depend on turbine pumps to emulsify ASA, the mean (particle) diameter values, ("MDV"), are almost always greater than 1 micron and usually average 2–3 microns, primarily because the emulsifier would be destroyed before the small particle size can be reached. Particle sizes in excess 4–5 microns are not an unusual event when produced by this methods. While the critical diameter (maximum particle size) value is not often discussed, most industry experts would agree that an ASA particle mean diameter value in excess of 5 microns would be unacceptable.

It is essential to create a high shear experience for the ASA in order to produce smaller particle sizes. The greater the shear, the smaller the particles. Fortunately, ASA is not shear sensitive and is not affected by high levels of shear. Therefore, there is no question about the great amount of shear to which the ASA is exposed when subjected to high pressure regenerative turbines and the like.

However, this is not equally true of the emulsifier ("starch"). The polymeric emulsifier is a shear sensitive compound which sustains damage in the turbine because the shear is set too high in order to achieve an ASA particle size reduction. Pressure drops in excess of 20 psi is all that is required to degrade certain synthetic polymer emulsifiers such as polyamines. Even the more shear resistant polyacrylamides suffer irreparable damage at pressures above 75–80 psi. Therefore, once the ASA and starch are mixed, the upper limit of shear is a point before the starch molecules begin to break up. This point is usually found by laboratory tests. The ideal mixing shear level is where the output product produces the smallest particle size with the highest emulsion viscosity.

Since alkaline paper making became more prominent in the 1970s and 1980s, the quality of ASA sizing programs have increased primarily through an improvement in the control of the particle size. As the average particle size dropped, the overall runability of the paper machine improved. Yet, heretofore, the best current technology has not been able to improve the ASA emulsion to provide a mean diameter value of particle size very much below 2 microns. Since the reduction of particle size improves the quality of the ASA program, a further reductions of particle size to sub-micron levels is beneficial. Without the benefit of sub-micron capabilities, it appears that a further enhancement to the ASA sizing programs cannot be fully evaluated.

The quality of the emulsion coming from the emulsification unit is established by the flow control of the ASA, emulsifier and water going to the unit. An increased flow of any of the emulsion components changes the particle size dramatically. Thus, pumps rated for, say 10 to 30 gpm, may be throttled back to 1 to 3 gpm in order to give the emulsion more residence time in the pump head so that it may be more properly sheared. In actual mill environments, flow variations and random changes in the particle size may be commonplace. Changes in the cooked starch viscosity can also impact particle size due to the adverse effect that viscosity has on a flow through turbine pumps.

The ASA emulsion quality is largely dependent on the particle size of the colloidal ASA droplets. Particle counters, particle size analyzers, and microscopes are available to estimate the emulsion particle size. While these tools are effective, they are also tedious and more importantly, intermittent, so that there is no continuous monitoring of production. Heretofore, samples had to be drawn from the emulsification unit and prepared in the mill laboratory in order to determine particle size. With such an intermittent testing, any changes in the quality of the emulsion on-line would not be detected in time to prevent at least some poor sizing performance on the paper machines.

Most emulsification units must provide relatively large horsepower driven pumps relative to their flow throughput in order to attain the desired shear. This is due in part to the difficult nature of blending two viscous liquids with each other and in the proper ratios. Sophisticated control systems essential to maintaining these critical ratios are, to say the least, very costly. When combined with their control systems, the large emulsifier systems may cost well over the hundred thousand dollar mark.

Therefore, an emulsification system that overcomes the many design flaws of existing technology is highly desirable.

Accordingly, an object of the invention is to provide a system which routinely introduces particles having sizes in the sub-micron region without subjecting the emulsifier to high pressure drop.

Another object of the invention is to provide a system less sensitive to variations in emulsifier flow rates and viscosity changes.

Yet another object of the invention is to provide a system with continuous on-line emulsion quality reporting capability.

A further object of the invention is to provide a system that is compact, and cost effective.

In keeping with an aspect of the invention, the emulsification of the ASA occurs in one stage. The ASA is injected through a special high pressure, atomizing nozzle into a flowing stream of starch (or other emulsifier). The high pressure breaks up or atomizes the ASA into minute particles that are evenly distributed to form a nearly perfect oil in water emulsion. By controlling the nozzle pressure, the proper particle size can be produced quite easily.

BRIEF DESCRIPTION OF DRAWINGS

A preferred embodiment of the invention is shown in the attached drawings, in which.

Preferably, the system comprises a variable speed low pressure starch metering pump, a variable speed high pressure ASA metering pump and high pressure nozzle assembly, an injection manifold which brings the starch and the ASA (nozzle) flow together, an ASA pressure regulator valve, a control panel with various electronic control and readout devices, an assortment of pressure gauges, flowmeters, line strainers etc., and an optical monitoring device that uses a coherent (laser) light source to continuously measure and validate the quality Of the ASA emulsion.

Figure 1:
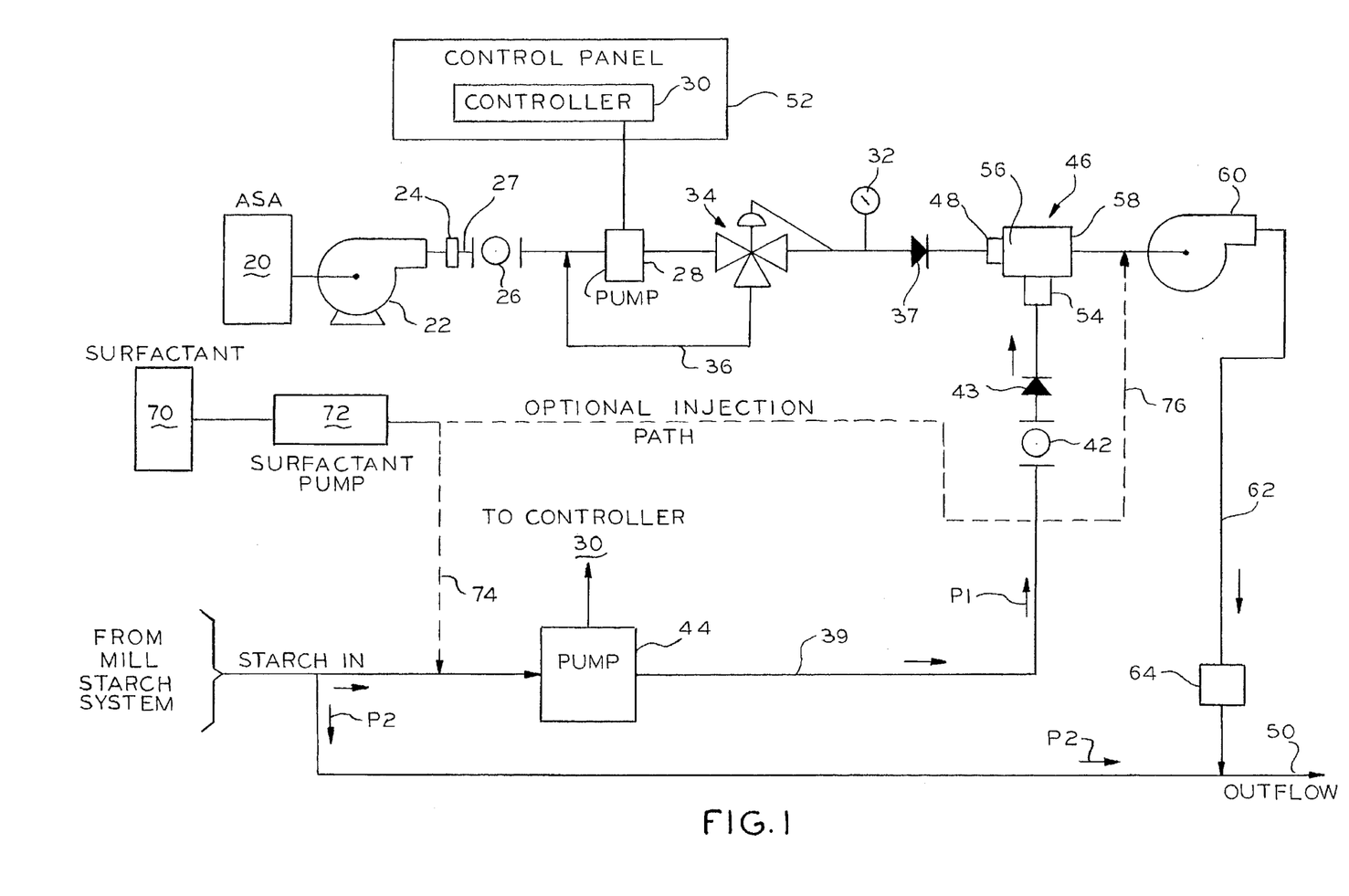
FIG. 1 is a block diagram of the inventive system.

More particularly, the inventive system, shown in FIG. 1, has a suitable tank 20 which stores the ASA blended with a surfactant in the range of 0.5–4% by weight. A centrifugal pump 22 delivers the mixture to a 100-mesh strainer 24. Pump 22 provides a positive head to pump 28 in the range of 10–60 psi.

A pressure gage 26 gives a continuous reading of the ASA pressure in line 27. A high pressure pump 28 raises the pressure of the ASA under the control of an AC variable speed control circuit 30. The pump 28 is preferably a positive displacement multi-piston type pump designed to deliver 4 gpm at 3000 psi. The high pressure ASA pump is a readily available commercial item manufactured by the Cat Pump Company of Minneapolis, Minn. An unexpected benefit of this pump and system design is the extremely low service demand on the high pressure ASA pump 28. Due to its ability to maintain a flat line pressure output which is independent of its speed, the pump is able to routinely perform at 4 percent of its design capacity. In actual operation, the pump shaft speed never exceeded 150 RPM or approximately 1/20th of its design range. This translates into long and extremely reliable service.

The output of pump 28 is directed past a pressure gage 32 that measures up to 3,000 psi. A pressure regulator 34 and unloader valve maintains the high pressure, and redirects some outflow from pump 28 back through pipe 36 and into the input of the high pressure pump 28. A check valve 37 prevents a back flow from the starch line contaminating the pristine ASA mixture.

Starch is transmitted from any suitable source (such as a mill) via a line 39 and any suitable Valves to an emulsifier flow meter or meters (not shown). A starch pump 44 delivers the starch through line 39 at a rate in the order of 0–10 gpm.

A three port injector manifold 46 has a nozzle 48 in one input port which delivers 512 ml/min at 2,500 psi. The nozzle 48 sprays and atomizes the ASA into a fine particle mist which is mixed with the starch entering the manifold port 54. The size of the particles depends upon the differential across the nozzle 48. The preferred pressures provide a back pressure of about 250–2500 psi. The preferred range of nozzle orifice sizes is 0.0110–0.15-inch, and the preferred size is 0.0135-inch.

Large particles sizes are obtained by simply adjusting pressure regulator 34 to lower the pressure differential across nozzle 48. Conversely, smaller particle sizes are easily obtained by increasing the nozzle pressure differential. The nozzles are designed and manufactured by Spraying Systems of Wheaton, Ill. and sold under the name "Spray Dry."

These nozzles are specially designed for the rigors of high pressure service and, more importantly, ultra fine spray characteristics. The results of various tests are set forth in FIGS. 3 and 4.

In one example, the nozzle 48 selected for service was the spraying system, model SK, rated to provide 3.4 to 151 gph and to operate at up to 7000 psi. Special tungsten carbide inserts insure long service at high pressures. The manufacturer (Spray Systems) expect this nozzle application to have an effective service life of 2 to 3 years.

In one example, the emulsification occurs when the ASA is injected via nozzle 48 at 46 and at pressures from 1000 psi to 3000 psi and eventually into an outflowing portion of the starch stream at output port 58 which is under little or no pressure. The flow rate of the starch stream is preferably adjusted to have a speed in the approximate range of 0.5 to 30 gpm, with 1–10 gpm preferred.

The flow of starch through pipe 39 may be under control of a positive displacement low pressure starch pump, such as 44, which may be in communication with the variable motor speed drive controller 30 housed in the main control panel. A first portion P1 of the starch stream is diverted through flow meter 42, and a check valve 43 to the manifold 46. The pump 44 is run at a speed which controls the ratio of ASA to starch at the output. For example, if the desired ratio of ASA to starch is 1:8, the pump 44 is run at a speed which delivers eight parts of starch at 54 for each part of ASA that is received at nozzle 48. The treated emulsion is delivered from pipe 50 to whatever following equipment that may use the outflow. A laser sensor 64 (described in U.S. Pat. No. 5,323,017) controls the system to hold the outflowing stream at substantially optimum particle conditions.

A flowmeter 42 between the outlet of the starch metering pump 44 and the injection manifold 46 precisely measures the flow of starch into the second input port 54 of the injection manifold, the flow rate being controlled by pump 44. A flowmeter readout may be displayed in terms of gpm at a main control panel 52. The preferred pump system is a readily available commercial item manufactured by Norchem Industries of Willowbrook, Ill.

In operation, the blend of ASA and surfactant, which may be stored in a large vessel 20 or the like, is gravity fed or pumped through in-line filters or strainers 24 designed to trap foreign particles before they can lodge in the high pressure feed circuit. Immediately following the filters, flowmeter 26 is located upstream of the high pressure metering pump 28. The readout of flowmeter 26 is also displayed in GPM at the main control panel 52. The pump motor is in communication with a variable speed drive 30 associate with the main control panel 52.

The discharge of high pressure ASA pump 28 is directed through a pressure regulating/unloader valve 34 which is located upstream of the injection manifold 46. There is a bypass relief line 36 on the pressure regulator/unloader valve which is returned to a point downstream of the inlet ASA flowmeter 26, but prior to or at the inlet of the high pressure ASA metering pump 28. A pressure gauge 32 is located between the pump 28 discharge and the injection manifold 46 to provide precise nozzle pressure readings. The injection manifold assembly 46 comprises three ports including one 56 with a special purpose high pressure spray nozzle. The manifold 46 receives the starch solution in a second port 54. The mixture of ASA and emulsion discharges out of the third and output port 58.

From there, the emulsion goes through a high speed centrifugal mixing pump 60 and out a pipe 62 to meet the part P2 of the stream of starch flowing through sensor 64 to the system output 50. The pump 60 is used in varying degrees of activity depending primarily upon how much surfactant is included within the stream in pipe 39. Ideally, the surfactant should not exceed 4% by weight of the mixture. Moreover, the speed and pressure of the mixing pump 60 is kept below the level which would reduce the effectiveness of the emulsifier by degrading substantial amounts of the emulsifier in response to energy imparted by said mixing pump. Ideally, the pump 60 is operated at a minimum rate to keep the system simple.

The starch to ASA ratio is set by adjusting the flow rate of the starch solution into port 54. The initial ratio in pipe 62 is 8:1 (8 parts starch, 1 part ASA). After the dilution when the streams in pipes 39, 62 combine, the ratio is 30:1. The flow rate of the ASA is regulated by the nozzle orifice and the pressure differential across the nozzle; therefore, the particle size is adjusted by setting the nozzle pressure at 34. An operator merely sets the starch pump 44 at a desired flow rate and adjusts the ASA pump pressure to produce the proper particle size for a high quality emulsion. Because the particle size is a function of the injection pressure, fluctuations in the starch flow and viscosity at input port 54 are unimportant.

A pilot system was constructed to test the efficacy of this invention. Tests were conducted to provide a laboratory verification of ASA emulsion particle size. The initial tests substituted water for starch to define the worst case condition for emulsification. City water containing approximately 220 PPM total hardness was used in this evaluation. The water flow rate was set at 4.0 gpm and the ASA was metered in at 512 ml/min at 2400 psi. This flow rate was chosen to closely approximate actual paper machine dosages. Samples were drawn and microscopically evaluated within 5 minutes.

A slide was prepared using a drop of the freshly prepared emulsion and evaluated under a microscope. The microscope was a Bausch and Lomb laboratory grade monocular design, fitted with a micrometer disc reticle. Optical measurements were made at 1000×magnification with an oil immersion objective. The overall scale in the field of view was 10 microns with graduation marks at the 1, 0.5, and 0.1 micron places. The combined results of the first tests (a total of three tests were run) indicated more than 50% of the particle sizes were at or below 1.0 microns. The remaining percent were between 0.1 and 3 microns. The emulsion stability was incredible considering that no emulsifier was used.

Control means are provided for enabling a continuous production run. Primarily, the prior art used non-continuous sampling as their only available means to verify the quality of the emulsion. At sensor 64, the inventive system provides the EPIC (Enhanced Polymer Imaging Controller) of U.S. Pat. No. 5,323,017 to continuously monitor the quality of the emulsion. The instrument is manufactured by Norchem Industries of Willowbrook, Ill. The EPIC controller uses a laser to apply a combination of light scatter and absorption principles to establish a spatial distribution of polymer composites which accurately corresponds to particle size and particle distribution. This instrument will detect instantaneous changes to the ASA particle size, which can be displayed at control panel 52.

Because the instrument scans the emulsion with coherent (laser) light and monitors only selective wavelengths, it can be fine tuned to look for particles within a specific refractive index in an extremely narrow bandwidth (5–20 nm). Because the refractive index of a substance varies for different wavelengths, conventional light scattering instruments are not reliable. Unlike turbiditmeters or nephelometers which use a white light (thermal radiation source), the laser eliminates all refractive index differences for all the wavelengths except those emanating from the source. All that remains to affect the light scatter, is the particle size and shape (distribution).

Various tests were run to determine the effect of nozzle size and the pressure across the nozzle.

Figure 2:
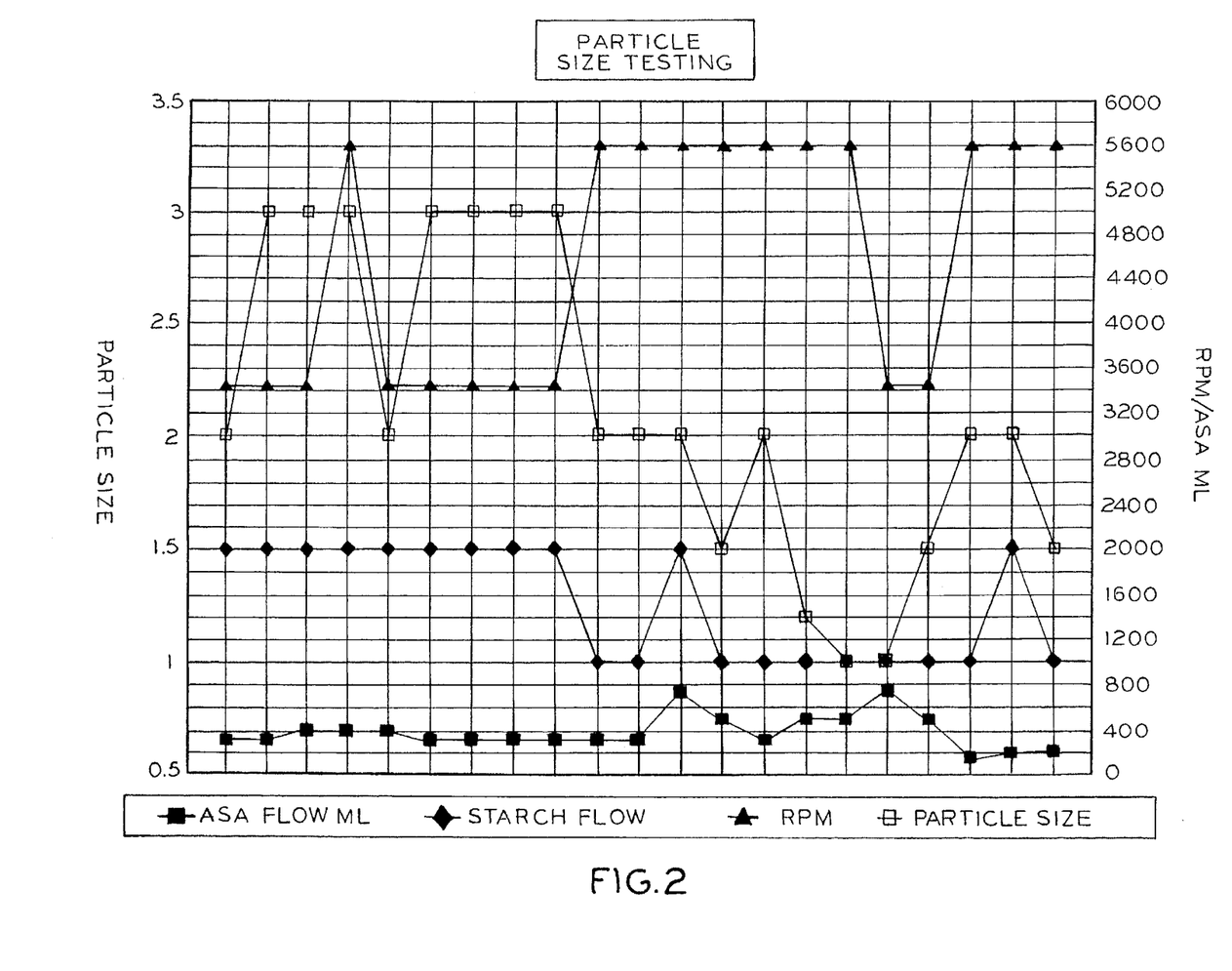
FIG. 2 is a graph showing changes in ASA particle size as a function of changes in pump speed.

FIG. 2 shows the effect of pump 60 upon particle size. A key to symbols used is included in FIG. 2. The revolutions per minute of the mixing pump 60 are shown by a scale on the right of FIG. 2 and are shown along a line marked by triangles at the top of FIG. 2. The ASA flow is shown by a line at the bottom of the graph and identified by solid squares. The amount of starch flow is shown in next to the bottom line and identified by diamonds.

The important feature of FIG. 2 is particle size shown by a line marked by hollow squares. The particle size is identified by the scale on the left of FIG. 2. It is apparent that, for this particular test run, the best operating conditions and the smallest particle size occurred when the mixing pump 60 was operating at 3400 RPM, the ASA flow rate was a little higher than normal, and the starch flow rate was at its lowest point.

FIG. 2 is not supposed to tell the best operating parameters for all uses of the system. Rather, it is designed to show the test data to be taken and how the system operator would go about using that data to select the various system settings for operating the system.

Figure 3:
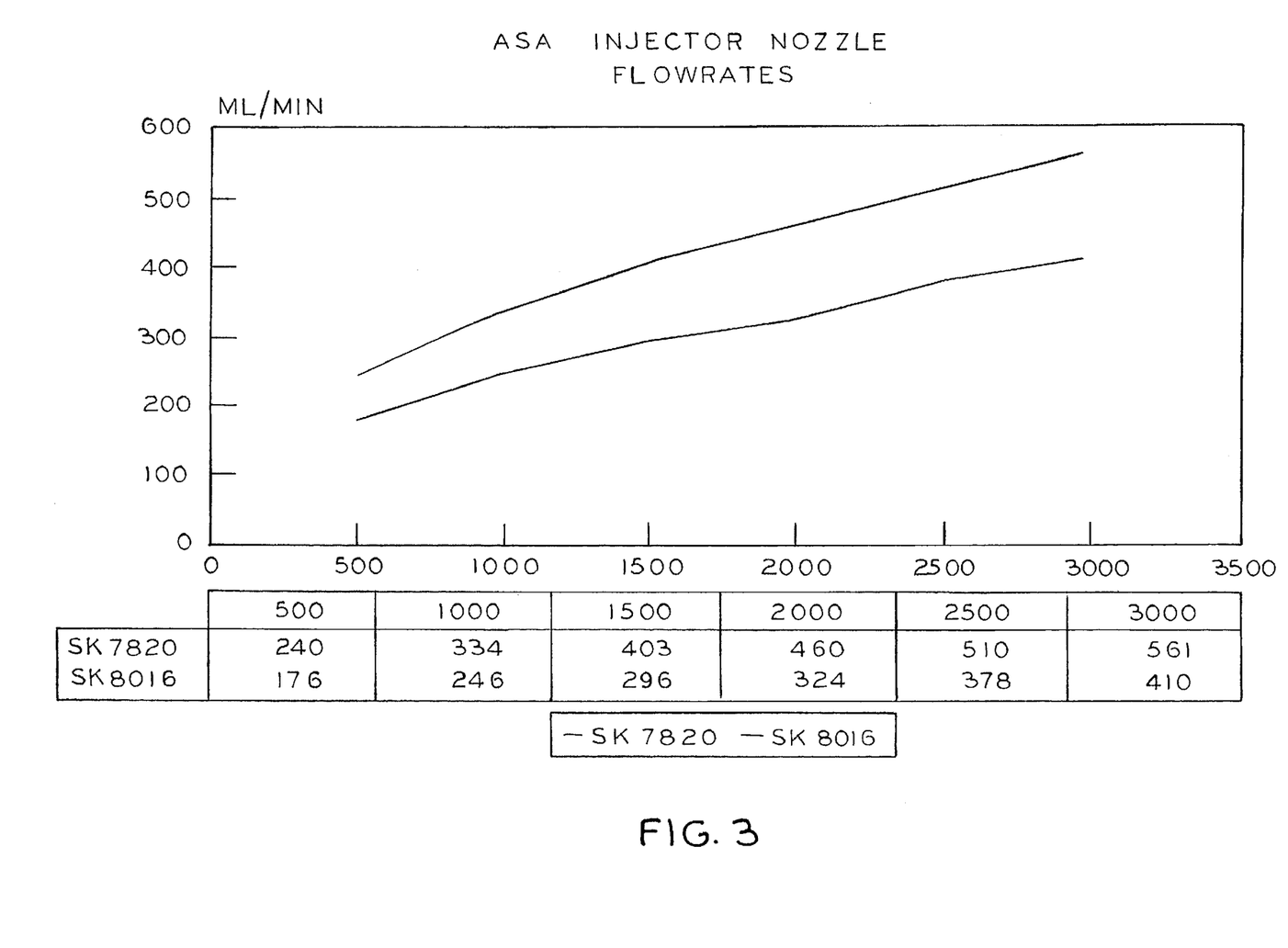
FIG. 3 is a graph which shows ASA injector nozzle flow rates.

FIG. 3 is useful for selecting the size of the orifice in nozzle 48 to be used for any given material. The size of the orifice in nozzle 48 determines the ASA flow rate, or amount in milliliters per minute, that is delivered as the pressure across the nozzle 48 increases from 500–3500 psi under the control of pressure regulator 34. The graph shows measurements taken for two nozzles here designated SK7820 and SK8016. Here again, FIG. 3 is designed to show how one goes about selecting the nozzle size for the desired operating point shown in FIG. 2.

Figure 4:
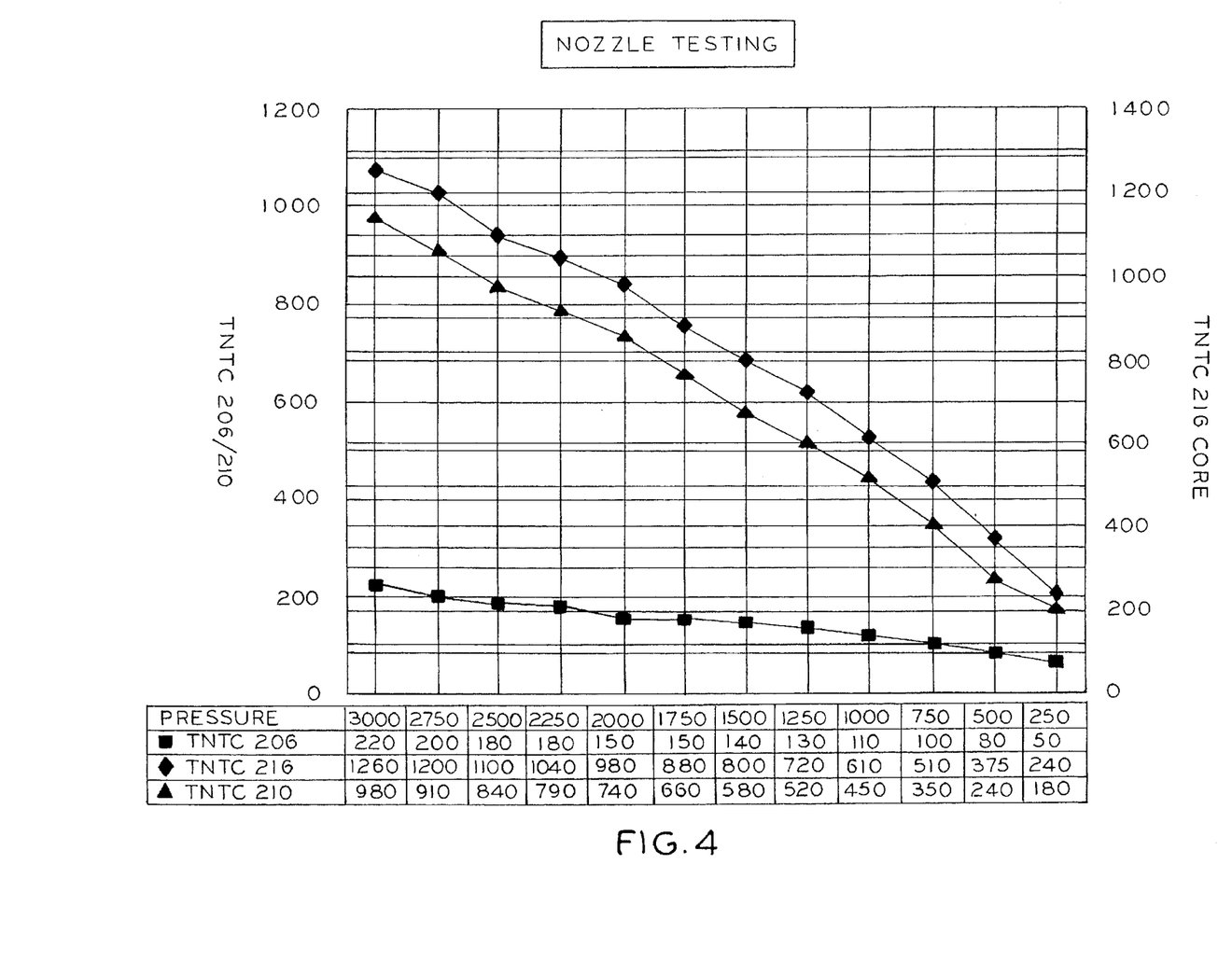
FIG. 4 is a graph which shows variations in a variety of nozzle flow rates as a function of variations in up stream pressure.

FIG. 4 shows yet another test which was run in order to select the proper nozzle. The lines are marked by symbols which identify how the nozzles react to changes in the pressure (noted on the bottom of the chart) set by pressure regulator 34. The numbers on the vertical scale indicate the milliliter per minute flow of nozzles TNTC206 nd TNTC210 on the left and of nozzle TNTC216 on the right. Again, the purpose of the chart of FIG. 4 is to show how one goes about selecting the proper nozzle for any given run of ASA and starch.

One of the problems is that when the inventive system is purchased, one does not know in advance exactly what component materials will be processed during the lifetime of the system. For example, the starch may be made from any of many different feed streams. There are a number of different ASA's with a great variety of molecular weights or other wide variances. There are thought to be thousands of different surfactants, each with its own particular characteristics.

In theory, at least, the materials which are processed by the inventive system may use any combination of these and perhaps other component materials. Therefore, to provide a system with greater flexibility, parts of the inventive system may be connected in a number of different ways for introducing and handling the various component materials. In FIG. 1, the solid lines show the preferred connections for introducing the component materials in a preferred sequence. The dashed lines show alternative connections which may modify the preferred system. Preferably, the various connections are made by opening and closing valves (not shown).

Some surfactants do not mix directly with the ASA, as well as they should, but do mix well with the starch, and that starch/surfactant mixture will combine with the ASA. Sometimes the surfactant mixes better with pure ASA. Sometimes the surfactant mixes better with a combination of starch and ASA.

Therefore, to provide for a number of optional arrangements, the material in tank 20 may be filled with pure ASA. A totally separate tank 70 may be provided for holding a surfactant completely separate from the ASA. A suitable pump 72 may deliver the surfactant under a controlled amount of pressure so that the proper ratio of surfactant to starch appears in the mix at output 50. When the nature of the component materials are such that the surfactant mixes best with pure starch, pump 72 delivers the surfactant directly into the inflowing starch feed stream via line 74. When the surfactant mixes best with the atomized ASA, pump 72 delivers the surfactant to the input of pump 60 via line 76. An adjustment of the starch flow or amount of flow over line 39 may cause the surfactant introduced via line 76 to combine with a stream of almost any reasonable ratio of ASA to starch which flow out of the manifold 46.

In each case, the ratio of ASA, surfactant, and starch is preferably set by adjusting the relative speeds of pumps 28, 44 and 60. While the ideal for most product is to have a 1:8 ratio of ASA to starch in line 62, and a ratio of 1:30 at outlet 50, the specific ratio may vary for any given product.

Those who are skilled in the art will readily perceive how to modify the invention. Therefore, the appended claims are to be construed to cover all equivalent structures which fall within the true scope and spirit of the invention.

The claimed invention is:

1. A method of preparing a polymer alkenyl succinic anhydride ("ASA") comprising the steps of:
   A. supplying a blend of surfactant and ASA;
   B. imparting a high pressure and high shear to said blend of a surfactant and ASA;
   C. feeding back a first portion of said blend from an output of step B to an input of step B in order to recirculate said blend through said high pressure and said high shear step B;
   D. feeding a second portion of said output from step B to a first input of a manifold via a nozzle for atomizing said blend, said atomized blend appearing within said manifold;
   E. feeding a first stream of an emulsifier into a second input to said manifold, said atomized blend combining with said first stream of said emulsifier to form a mixture of ASA, surfactant, and emulsifier within said manifold; and
   F. feeding said mixture combined in step E into a second stream of said emulsifier to provide an outflow of prepared ASA, said outflow having a ratio of ASA to emulsifier set by the relative volumes of said first and second streams of said emulsifiers.

2. The method of claim 1 wherein said step (F) includes the step of feeding said combined mixture through a high speed mixing pump, said high speed mixing pump operating below a speed and pressure which reduces the effectiveness of the emulsifier by degrading substantial amounts of said emulsifier in response to energy imparted by said mixing pump.

3. The method of claim 1 wherein step (D) comprises a formation of a substantial majority of ASA particles having a particle size in the range of 0.25–2 μ.

4. The method of claim 1 wherein step (D) comprises formation of ASA particles having a particle size less than 1 μ.

5. The method of claim 1 wherein said surfactant of step (A) is in the range of 0–4% by weight of the blend of surfactant and ASA.

6. The method of claim 1 wherein the ratio of ASA to emulsifier is 1:8 in step E and is 1:30 in step F.

7. A method of preparing a polymer alkenyl succinic anhydride ("ASA") comprising the steps of:
   (A) combining an emulsifier and ASA, said ASA comprising a blend of ASA and a surfactant, with a substantial portion of said ASA being formed into particles having a particle size within the range of 0.25–2 μ, said step (A) processing said ASA into particles further comprising the steps of subjecting said blend of ASA and surfactant to very high pressure and forcing said pressurized blend of ASA and surfactant through a nozzle having an orifice small enough to atomize said blend;
   (B) diluting the combination of step (A) with a first stream of pure emulsifier, spraying said atomized blend into said first stream of pure emulsifier; and
   (C) carrying out said dilution of step (B) with a mixing device that imparts a shear force which is less than that which reduces the effectiveness of said emulsifier by degrading substantial amounts of said emulsifier.

8. The method of claim 7 in which a second stream of said emulsifier is used and further comprising step of mixing said first and second streams of emulsifier to dilute the amount of ASA relative to the amount of emulsifier, said mixing being carried out at a shear level which is less than a shear level that reduces the effectiveness of said emulsifier, wherein said first and second streams of emulsifier may be combined in a selected one of a plurality of different percentages in order to adjust the ratio of ASA to emulsifier in the mixed stream.

9. The method of claim 8 wherein the ratio of ASA to emulsifier is 1:8 in said first stream and is 1:30 after said dilution by said mixing of said first and second streams.

10. The method of claim 7 wherein step (A) comprises the steps of blending said ASA and a surfactant, pressurizing said blend to about 3000 psi and passing said pressurized blend through a nozzle, said nozzle having an orifice diameter selected from a range of about 0.0135–0.015 inch.

11. The method of claim 10 wherein the diameter of said nozzle orifice is 0.0135 inch.

* * * * *

UNITED STATES PATENT AND TRADEMARK OFFICE
CERTIFICATE OF CORRECTION

| | | |
|---|---|---|
| PATENT NO. | : 5,653,915 | Page 1 of 1 |
| APPLICATION NO. | : 08/438411 | |
| DATED | : August 5, 1997 | |
| INVENTOR(S) | : Dennis G. Pardikes | |

It is certified that error appears in the above-identified patent and that said Letters Patent is hereby corrected as shown below:

On the Title Page, Item -54-
The Title of the Invention is changed from "METHOD OF PREPARING POLYMER SUCCINIC ANHYDRIDE" to -- METHOD OF PREPARING AN ALKENYL SUCCINIC ANHYDRIDE EMULSION --.

Signed and Sealed this

Twentieth Day of January, 2009

JON W. DUDAS
*Director of the United States Patent and Trademark Office*

UNITED STATES PATENT AND TRADEMARK OFFICE
CERTIFICATE OF CORRECTION

PATENT NO.        : 5,653,915                                    Page 1 of 1
APPLICATION NO. : 08/438411
DATED             : August 5, 1997
INVENTOR(S)       : Dennis G. Pardikes

It is certified that error appears in the above-identified patent and that said Letters Patent is hereby corrected as shown below:

On the Title Page, Item -54- and Column 1, lines 1 and 2
The Title of the Invention is changed from "METHOD OF PREPARING POLYMER SUCCINIC ANHYDRIDE" to -- METHOD OF PREPARING AN ALKENYL SUCCINIC ANHYDRIDE EMULSION --.

This certificate supersedes the Certificate of Correction issued January 20, 2009.

Signed and Sealed this

Tenth Day of February, 2009

JOHN DOLL
*Acting Director of the United States Patent and Trademark Office*